United States Patent
Goldfarb et al.

(10) Patent No.: US 9,513,199 B2
(45) Date of Patent: Dec. 6, 2016

(54) RAPID FREEZE-QUENCH DEVICE AND METHODS OF USE THEREOF

(71) Applicant: YEDA RESEARCH AND DEVELOPMENT CO.LTD, Rehovot (IL)

(72) Inventors: Daniella Goldfarb, Rehovot (IL); Royi Kaufmann, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 51 days.

(21) Appl. No.: 14/178,310

(22) Filed: Feb. 12, 2014

(65) Prior Publication Data

US 2014/0227685 A1    Aug. 14, 2014

Related U.S. Application Data

(60) Provisional application No. 61/763,499, filed on Feb. 12, 2013.

(51) Int. Cl.

| | |
|---|---|
| *G01N 1/42* | (2006.01) |
| *B01L 7/00* | (2006.01) |
| *B01F 5/06* | (2006.01) |
| *B01F 13/00* | (2006.01) |
| *B01L 3/00* | (2006.01) |

(52) U.S. Cl.
CPC ............... *G01N 1/42* (2013.01); *B01F 5/0647* (2013.01); *B01F 13/0059* (2013.01); *B01L 7/50* (2013.01); *B01L 3/5027* (2013.01); *B01L 2200/0636* (2013.01); *B01L 2200/0673* (2013.01); *Y10T 436/25* (2015.01)

(58) Field of Classification Search
CPC ...... G01N 1/42; B01F 5/0647; B01F 13/0059; B01L 7/50; B01L 2200/0673; B01L 3/5027; B01L 2200/0636; Y10T 436/25
See application file for complete search history.

(56) References Cited

PUBLICATIONS

Ballou et al.; "Practical Rapid Quenching Instrument for the Study of Reaction Mechanisms by Electron Paramagnetic Resonance Spectroscopy", Analytical Chemistry, vol. 46, No. 9, Aug. 1974, pp. 1248-1253.
Ballou; "Freeze-quench and chemical-quench techniques", Methods in Enzymology 54 (1978) 85-93.
Belevich et al.; "Electron Transfer in Respiratory Complexes Resolved by an Ultra-Fast Freeze-Quench Approach", Methods in Enzymology, vol. 456 (2009) 75-93.

(Continued)

*Primary Examiner* — Lore Jarrett
(74) *Attorney, Agent, or Firm* — Mark S. Cohen; Pearl Cohen Zedek Latzer Baratz LLP

(57) ABSTRACT

This invention provides mixing, reaction and ejection devices for small volume samples. This invention also provides cooling devices, sample preparation apparatuses and sample preparation methods for studying chemical and biological reactions. The mixing, reaction and ejection devices of this invention allow ejection of small volume liquid samples from a microfluidic channel. Cooling devices of the invention enable serial cooling and collection of samples in an efficient and accurate manner. This invention also provides apparatuses comprising the mixing, reaction and ejection devices and cooling devices. This invention provides methods of using the novel devices and apparatuses.

45 Claims, 6 Drawing Sheets

(56) References Cited

PUBLICATIONS

Bray; "Sudden Freezing as a Technique for the Study of Rapid Reactions", Biochem. J 81 (1961) 6.
Burdi et al.; "The Core Structure of X Generated in the Assembly of the Diiron Cluster of Ribonucleotide Reductase: 17O2 and H217O ENDOR", J. Am. Chem. Soc. 120 (1998,) 12910-12919.
Cherepanov et al.; "Microsecond freeze-hyperquenching: development of a new ultrafast micro-mixing and sampling technology and application to enzyme catalysis", Biochimica et Biophysica Acta 1656 (2004) 1-31.
Dockter et al.; "Refolding of the integral membrane protein light-harvesting complex II monitored by pulse EPR", Proc. Nat. Acad. Sci. USA 106 (2009) 18485-18490.
Egawa et al.; "Design and Evaluation of a Passive Alcove-Based Microfluidic Mixer", Anal. Chem. 2009, 81, 1622-1627.
Goldfarb et al.; "HYSCORE and DEER with an upgraded 95 GHz pulse EPR spectrometer", J. Magn. Reson. 194 (2008) 8-15.
Kaufmann et al.; "Developing a novel rapid microfluidic Freeze-Quench Device for trapping intermediates of enzymatic reactions for EPR analysis", Abstract published on Jul. 1, 2012 at Euromart meeting.
Kaufmann et al.; "Developing a novel rapid microfluidic Freeze-Quench Device for trapping intermediates of enzymatic reactions for EPR analysis", poster displayed on Jul. 1, 2012 at Euromart meeting Jul. 4, 2012.
Kim et al.; "Rapid Freeze-Quench ENDOR Study of Chloroperoxidase Compound I: The Site of the Radical", J. Am. Chem. Soc. 128 (2006) 5598-5599.
Lassmann et al.; "An advanced EPR stopped-flow apparatus based on a dielectric ring resonator", J. Magn. Reson. 172 (2005) 312-323.
Lin et al.; "Ultrafast Microfluidic Mixer and Freeze-Quenching Device", Anal. Chem. 2003, 75, 5381-5386.
Manzerova et al.; "Investigating the intermediates in the reaction of ribonucleoside triphosphate reductase from Lactobacillus leichmannii: An application of HF EPR-RFQ technology", J. Magn. Reson. 213 (2011) 32-45.
Nguyen et al.; "Micromixers—a review", J. of Micromechanics and Microengineering 15 (2005) R1-R16.
Pievo et al.; "A Rapid Freeze-Quench Setup for Multi-Frequency EPR Spectroscopy of Enzymatic Reactions", Chemphyschem., Dec. 16, 2013;14(18):4094-101.
Potapov et al.; "A Calibration Reaction for Rapid Freeze-Quench W-Band EPR", Appl. Magn. Reson. 37 (2010) 845-850.
Schmidt et al.; "Design, Implementation, Simulation, and Visualization of a Highly Efficient RIM Microfluidic Mixer for Rapid Freeze-Quench of Biological Samples", Appl Magn Reson (2011) 40:415-425.
Schunemann et al.; "Tyrosine Radical Formation in the Reaction of Wild Type and Mutant Cytochrome P450cam with Peroxy Acids", J. Biol. Chem. 279, (2004) 10919-10930.
Suarez et al.; "An Oxyferrous Heme/Protein-based Radical Intermediate Is Catalytically Competent in the Catalase Reaction of Mycobacterium tuberculosis Catalase-Peroxidase (KatG)", J. Biol. Chem. 284 (2009) 7017-7029.
Takahashi et al.; "Folding of cytochrome c initiated by submillisecond mixing", Nat. Struct. Biol. 4 (1997) 44-50.
Tsai et al.; "An Improved Sample Packing Device for Rapid Freeze-Trap Electron Paramagnetic Resonance Spectroscopy Kinetic Measurements", Analytical Biochemistry 264, 165-171 (1998).

RAPID FREEZE-QUENCH DEVICE AND METHODS OF USE THEREOF

CROSS REFERENCE TO RELATED APPLICATIONS

This application claims priority from U.S. Ser. No. 61/763,499, filed Feb. 12, 2013, which is hereby incorporated by reference in its entirety.

FIELD OF THE INVENTION

This invention is directed to rapid freeze-quench devices and apparatuses. This invention is further directed to methods of use of rapid freeze-quench devices and apparatuses.

BACKGROUND OF THE INVENTION

Understanding the reaction mechanisms of enzymes is an important step towards designing inhibitors for therapeutic purposes and for biomimetic applications. Such reaction mechanisms involve kinetics that reveals the various steps of the reaction, the reaction rate constants and the associated activation energies. In addition, reaction mechanisms focus on identification of reaction intermediates and their structural transformations. Such transformations can be conformational changes of the enzyme, formation of enzyme-substrate complexes etc. A complete understanding of a reaction mechanism involves identification of reaction intermediates, evaluation of reaction kinetics and assessment of the sequence and rate of structural transformations. While the kinetic is usually studied by stop-flow techniques combined primarily with optical spectroscopic detection, the structural analysis often requires freeze quench approaches. In freeze quench approaches, snap shots of reaction intermediates are obtained by rapid freezing followed by spectroscopic analysis of the frozen sample. Spectroscopic analysis includes for example electron paramagnetic resonance (EPR) or extended X-ray absorption fine structure (EXAFS).

Rapid-freeze quench (RFQ)-EPR is an established method where two (or more) components are mixed at ambient temperature and after some delay the liquid is sprayed into a cold trap. The frozen particles are collected into an EPR tube for measurement. The standard time resolution of commercial RFQ apparatuses is currently in the ms range with a typical dead-times of about 5-10 ms. Shorter deadtimes (~200 µs) can be obtained with home-built setups, such as the tangential mixer set up. The deadtime is the shortest reaction time that can be accessed with the RFQ device.

RFQ-EPR is currently applied mostly to biological systems, specifically enzymatic reactions and the samples are usually analyzed by X-band (9.5 GHz) continuous wave (CW) EPR. Trapped samples were also subjected to interrogation by high resolution EPR techniques. One example is electron nuclear double resonance (ENDOR) which provides ligand hyperfine couplings that are essential for further characterization of the trapped intermediates. Recently, distance measurements by double electron-electron resonance (DEER) were also applied to freeze-quenched samples to follow protein folding.

High resolution X-band EPR techniques are usually less sensitive than CW EPR and therefore require large amount of sample for a complete set of measurements (e.g. 7-10 samples of ~50 µl, 0.1-1 mM, each). This causes a difficulty that prevents the routine combination of RFQ with such high resolution EPR techniques. One way to overcome this obstacle is by coupling RFQ with sensitive high field EPR spectrometers. For example, the sample volume for W-band (95 GHz) EPR in systems employing a cavity (e.g. Bruker commercial spectrometers) is ~2 µl with a concentration range comparable to that used for X-band. This is a ~20 fold reduction in sample amount compared to X-band measurements. This difference becomes most significant when a set of 7-10 samples is required for a complete RFQ experiment. Another advantage of high field EPR and ENDOR is their increased spectral resolution. Currently, efficient high field RFQ-EPR is unavailable, primarily because of the difficulty to handle small sample tubes (capillaries) and the lack of an apparatus offering high yield and efficient collection of small volume samples.

The first application of RFQ high-field EPR was reported by Schunemann et. al. where the reaction of cytochrome P450cam with peroxy acids revealed the formation of tyrosyl radicals as intermediates. The freeze quenched samples were subjected to CW EPR measurements at 95, 195 and 285 GHz. The mixing and freezing were done using a commercial system from Update Instruments. The collection system for W-band was modified to be suitable for working with fragile quartz capillaries. In this approach, although high resolution is obtained by the high field measurements, a large amount of protein is required and most of it is wasted. In another study, RFQ with conventional and high-field EPR was utilized to resolve a unique heme and radical intermediates in the reaction of *M. tuberculosis* KatG with hydrogen peroxide. The mixing was done by a commercial system (Update instruments) and the liquid was sprayed onto a set of two rotating copper wheels partially immersed in liquid nitrogen. A home-built platform immersed into liquid nitrogen was used for sample collection.

An effective RFQ apparatus for W- or D-band (140 MHz) EPR spectrometers that uses a cavity should be able to use microfluidic technology to take full advantage of the small sample volume needed. Such a set-up has been introduced by Lin et. al. for X-band application where the primary objective was to shorten the dead-time. A microfluidic mixer was used and the freezing was achieved by spraying the sample onto cold copper-beryllium rotating wheels. Another microfluidic RFQ set up for high field EPR with a modified design for a single sample collection on vertical copper rotating wheels has been recently reported by J. Manzerova et. al. in J. Mag. Res. 213 (2011) 32-45. The drawback of the sample collection used in this setup is that after each time point the rotating wheels have to be cleaned, and the dead-time reported was rather long (~30 ms). Further, the total amount of sample needed for a series of samples collected at different reaction times is not evident.

RFQ-EPR suffers from the difficulties of producing and manipulating small samples and from the inefficiency of sample freezing and sample collection processes in experiments that involve series of samples.

SUMMARY OF THE INVENTION

In one embodiment, this invention provides a microfluidic device comprising:
  a microfluidic channel comprising a first mixing part and a second reaction part, wherein said channel further comprises a first inlet and a second inlet;
  a product outlet, wherein said product outlet is attached to said microfluidic channel;

a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;

wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet.

In one embodiment, the first inlet and the second inlet are connected to an injection pump. In one embodiment, the pump is used to inject said first and said second materials through said inlets into said microfluidic channel. In one embodiment, the pump controls the flow rate of materials within the reaction part of the microfluidic channel.

In one embodiment, the gas inlet channel is connected to a pressurized gas cylinder. In one embodiment, the gas cylinder is used to deliver gas through said gas inlet channel and out of said gas compartment.

In one embodiment, this invention provides an apparatus for sample preparation, the apparatus comprising:
  a microfluidic device comprising:
    a microfluidic channel comprising a first mixing part and a second reaction part, wherein said channel further comprises a first inlet and a second inlet;
    a product outlet, wherein said product outlet is attached to said microfluidic channel;
    a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;
  wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet;
  a cooling device comprising:
    a translation element comprising a surface; and
    a cooling means;
  wherein said translation element is cooled by said cooling means;
  wherein said product outlet of said microfluidic device is placed in proximity to said cooling device such that material can be transferred from said microfluidic device onto different areas on said surface of said translation element.

In one embodiment, the translation element is motorized. In one embodiment, the translation element is movable around an axis, along an axis or a combination thereof. In one embodiment, the distance between the surface of the translation element and the product outlet channel, ranges between 2.5 mm and 7.5 mm.

In one embodiment, this invention provides a method of preparation of samples for analysis, said method comprising:

a. providing an apparatus for analysis, said apparatus comprising:
   a microfluidic device comprising:
     a microfluidic channel comprising a first mixing part and a second reaction part, wherein said channel further comprises a first inlet and a second inlet;
     a product outlet, wherein said product outlet is attached to said microfluidic channel;
     a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;
   wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet;
   a cooling device comprising:
     a translation element comprising a surface; and
     a cooling means;
   wherein said translation element is cooled by said cooling means;
   wherein said product outlet of said microfluidic device is placed in proximity to said cooling device such that material can be transferred from said microfluidic device onto different areas on said surface of said translation element.
b. cooling said translation element using said cooling means;
c. translating said surface of said translation element such that said top surface of said translation element remains at a constant vertical distance from said microfluidic device;
d. injecting a first reactant solution from said first inlet and a second reactant solution from said second inlet such that said first reactant and said second reactant get into contact at said mixing part and wherein said reactants are mixed within said mixing part and wherein said reactants at least partially react within said reaction part;
e. ejecting samples comprising at least partially reacted materials in a serial manner from said product outlet onto different areas of said surface of said translation element, wherein upon ejecting, the product solution is mixed with gas ejected from said gas compartment thus facilitating ejection of said product solution.

In one embodiment, the reaction time of the reactants is controlled by the injection rate of the reactants solutions. In one embodiment, the reaction time is in the millisecond (ms) range.

In one embodiment, the number of samples transferred from the microfluidic device to the surface of the translation element ranges between 1 and 100.

In one embodiment, the microfluidic device is connected to a motor. In one embodiment, the microfluidic device is moved horizontally with respect to the surface of the translation element. In one embodiment, by horizontally moving the microfluidic device with respect to the surface of the translation element, the samples are transferred to different areas on the surface of the translation element. In one embodiment, different samples ejected from the microfluidic device following different reaction times are serially collected on different areas of the surface of the translation element.

In one embodiment, the reaction time is controlled by injection flow rate.

In one embodiment, the sample ejected from the microfluidic device, is mixed with gas from the gas compartment and forms small droplets. In one embodiment, the sample comprising small droplets freezes upon contact with the surface of the translation element. In one embodiment, the sample freezes in small drops on the surface of the translation element.

In one embodiment, following sample transferring onto the surface of the translation element, the samples are transferred to capillaries. In one embodiment, transferring into capillaries is automated. In one embodiment, following transfer of samples to the capillaries, the capillaries are frozen in liquid nitrogen.

In one embodiment, the capillaries are transferred to an analysis instrument. In one embodiment, the analysis instrument comprises an optical spectrophotometer, a mass spectrometer, an NMR instrument, an instrument for magnetic analysis, an electrical properties analysis instrument, a surface analysis instrument, a microscope, a chromatography tool, an electrophoresis set up or a combination thereof.

In one embodiment, the analysis instrument is electron paramagnetic resonance (EPR) instrument.

In one embodiment, the method is used to study reaction mechanisms.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
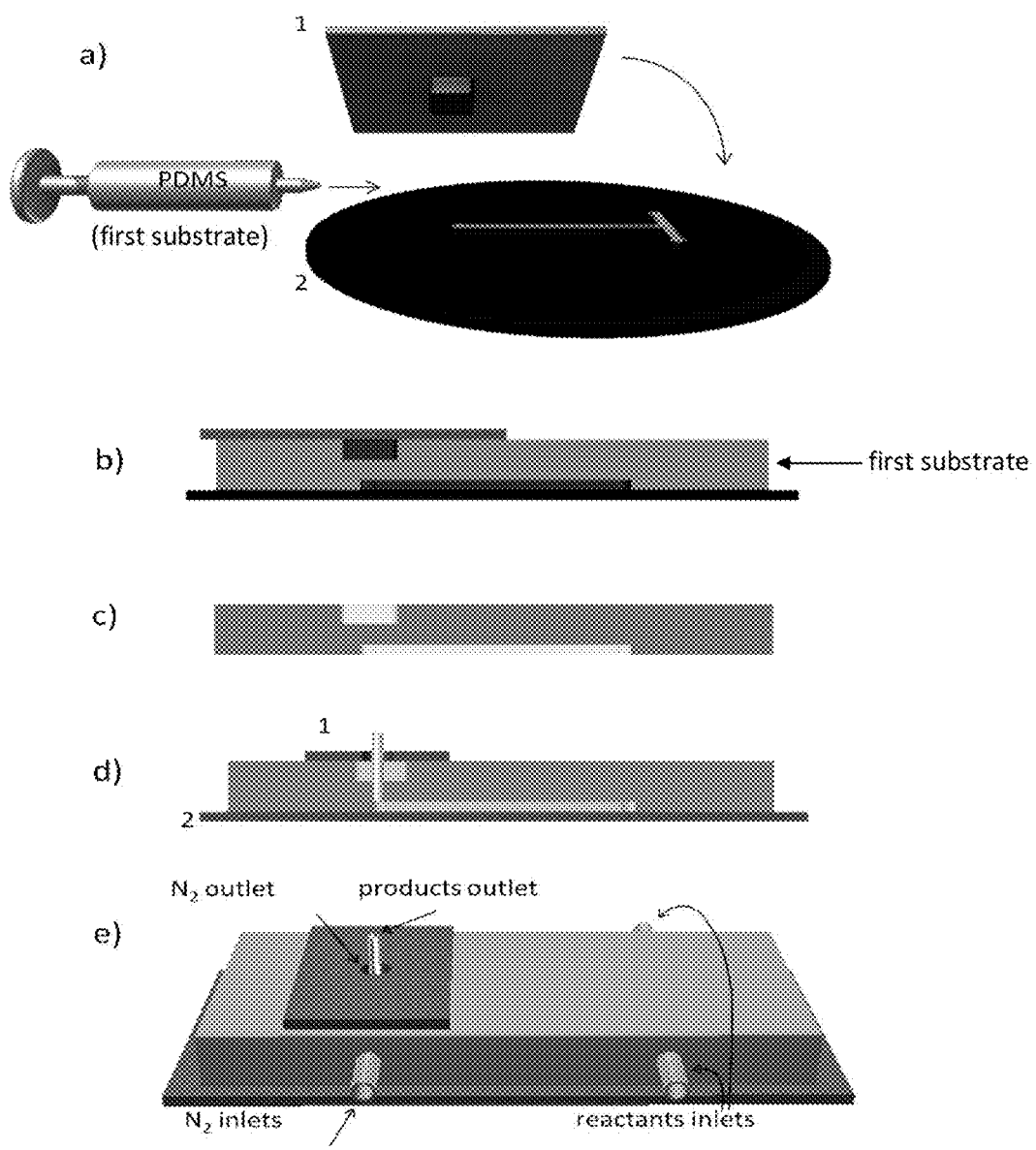
FIG. 1 is a description of the fabrication steps of a microfluidic device.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Rapid freeze quench electron paramagnetic resonance (RFQ)-EPR is a method for trapping short lived intermediates in chemical reactions and subjecting them to EPR spectroscopy for characterization. Two (or more) reacting components are mixed at room temperature and after some delay the mixture is sprayed into a cold trap and transferred into the sample tube. The small sample volume (~2 µl) needed for high field EPR spectrometers, such as W-band (~3.5 T, 95 GHz), that use cavities calls for the development of a microfluidic based RFQ-EPR apparatus. This is particularly important for biological applications because of the difficulties often encountered in producing large amounts of intrinsically paramagnetic proteins and spin labeled nucleic acid and proteins. This invention provides a dedicated microfluidic based RFQ-EPR apparatus suitable for small volume samples in the range of a few µl. The device is based on a microfluidic mixer and features a new ejection mechanism and a novel cold trap that allows collecting a series of different time points in one continuous experiment. The reduction of a nitroxide radical with dithionite, employing the signal of $Mn^{2+}$ as an internal standard was used to demonstrate the performance of the microfluidic RFQ apparatus.

In one embodiment, this invention provides a dedicated microfluidic based RFQ-EPR apparatus for W-band measurements, or for any other spectroscopic analysis tool that requires sample volumes in the µl range. The microfluidic mixer is based on a design fabricated from a polymer rather than silicon. This allows easy fabrication using in-house facilities. More importantly, this apparatus features a newly designed cold trap where all time points in a RFQ series are collected in one continuous experiment. The reduction of a nitroxide radical with dithionite, employing the signal of $Mn^{2+}$ as an internal standard is used to demonstrate an embodiment of performance of the system. This set-up features a dead-time of ~5 ms in one embodiment and is highly efficient in terms of sample use. The total volume needed for 7 time points in triplicates is <150 µl. The concentration required is a function of the yield and character of the paramagnetic center observed, the type of measurement performed, and the specifications of the spectrometer. For example, a W-band spectrometer requires C≥0.05 mM for DEER on either nitroxide or $Gd^{3+}$ spin labels.

In one embodiment, the temperature of the microfluidic device is controlled by contacting the microfluidic device with a heating source. In one embodiment, the heating source may comprise a heating plate or a heating tape adhered to at least one surface of the microfluidic device.

Devices and Apparatuses of the Invention

In one embodiment, this invention provides a microfluidic device comprising:
- a microfluidic channel comprising a first mixing part and a second reaction part, wherein said channel further comprises a first inlet and a second inlet;
- a product outlet, wherein said product outlet is attached to said microfluidic channel;
- a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;

wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet.

In one embodiment, the first and the second inlets comprise a first inlet channel and a second inlet channel. In one embodiment, the first inlet channel and the second inlet channel comprise a first end and a second end. In one embodiment, the first end of the inlet channels is connected to an injection pump(s). In one embodiment, the second end of the inlet channels is in contact with a first end of the microfluidic channel. In one embodiment, the inlets or the inlet channels transfer material(s) from a reservoir or from any other sample source into the microfluidic channel and the materials are being mixed within the mixing part of the channel. In one embodiment, when different materials are introduced to the mixing part of the channel from the at least two inlets or from the at least two inlet channels, the materials get in contact and mix within the first mixing part and react with each other within the second reaction part of said microfluidic channel thus forming a product (or products) of a reaction within the reaction channel. In one embodiment, the longer the time that the reacting materials spend in the reaction part of the channel, a larger amount of product may form within the reaction part of the channel In one embodiment, the longer the time that the reacting materials spend in the reaction part of the channel, more reaction steps may occur and different intermediates corresponding to the different reaction steps may form.

In one embodiment, the inlets to the microfluidic channel or the first end of the inlet channels is connected to a unit that allows pressure driven flow into and through the inlets/inlet channels, through the microfluidic channel or a combination thereof. In one embodiment, such unit comprises a pump. In one embodiment, the pump is a syringe pump. In one embodiment, the pump is used to inject the materials through the inlets into said microfluidic channel. In one embodiment, the term "inlet" and the term "inlet channel" are both used to describe the inlets through which a solution comprising species of interest is introduced into the microfluidic channel.

In one embodiment, the pump (injection pump) controls the flow rate of material(s) within the inlet channels. In one embodiment, the pump (the injection pump) controls the flow rate of material(s) within the microfluidic channel. In one embodiment, the pump (the injection pump) controls the flow rate of material(s) within the second reaction part of the microfluidic channel.

In one embodiment, flow rates within the second reaction part of the microfluidic channel range between 100 mm/s and 1000 mm/s. In one embodiment, flow rates within the microfluidic channel range between 200 and 300 mm/s. In one embodiment, flow rates within the microfluidic channel range between 10 and 10,000 mm/s. In one embodiment, flow rates within the microfluidic channel range between 50 and 500 mm/s. In one embodiment, flow rates within the microfluidic channel range between 500 and 1000 mm/s.

In one embodiment, the flow rate within the inlet channels, within the mixing part of the microfluidic channel, within the reaction part of the microfluidic channel or a combination thereof is an electroosmotic flow.

In one embodiment, the length of the microfluidic channel ranges between 0.5 cm and 4 cm. In one embodiment, the length of the microfluidic channel ranges between 1.0 cm and 3.0 cm. In one embodiment, the length of the microfluidic channel ranges between 0.5 cm and 1.5 cm. In one embodiment, the length of the microfluidic channel ranges between 2.0 cm and 6.0 cm. In one embodiment, the length of the microfluidic channel ranges between 0.1 cm and 2 cm. In one embodiment, the length of the microfluidic channel ranges between 1 cm and 10 cm. In one embodiment, the length of the microfluidic channel is 1 cm.

In one embodiment, the height of the microfluidic channel ranges between 10 µm and 100 µm. In one embodiment, the height of the microfluidic channel ranges between 25 µm and 75 µm. In one embodiment, the height of the microfluidic channel ranges between 1.0 µm and 20 µm. In one embodiment, the height of the microfluidic channel ranges between 40 µm and 60 µm. In one embodiment, the height of the microfluidic channel is 50 µm.

In one embodiment, the width of the microfluidic channel ranges between 10 µm and 150 µm. In one embodiment, the width of the microfluidic channel ranges between 50 µm and 100 µm. In one embodiment, the width of the microfluidic channel ranges between 10 µm and 100 µm. In one embodiment, the width of said microfluidic channel ranges between 1 µm and 50 µm. In one embodiment, the width of said microfluidic channel is 75 µm.

In one embodiment, the width of at least a portion of the microfluidic channel is constant. In one embodiment, the width of at least a portion of the microfluidic channel varies along the length of said microfluidic channel In one embodiment, the microfluidic channel is divided to two parts. In one embodiment, the first part is the mixing part and the second part is the reaction part. According to this aspect and in one embodiment, the mixing part of the microfluidic channel is not symmetric. In one embodiment, the width of the mixing part of the microfluidic channel varies along the channel. In one embodiment, the mixing part of the microfluidic channel is not straight but rather comprises a non-symmetrical "zig-zagged" shape as depicted in FIG. 2a.

In one embodiment, the non-symmetric mixing part of the microfluidic channel is used to enable efficient mixing of ingredients introduced from the at least two inlets. In another embodiment, other mixer geometries are utilized. According to this aspect and in one embodiment, the mixer comprises a small chamber. In one embodiment, at least one dimension defining the chamber is in the micrometer range.

In one embodiment, the second part (the reaction part) of the microfluidic channel is a continuation of the first part (the mixing part). In one embodiment, the second part of the microfluidic channel comprises a straight channel. In one embodiment, the straight channel comprises a constant width. In one embodiment, the straight reaction channel comprises a constant length. In one embodiment, the length of the reaction part of the microfluidic channel is used to estimate the reaction time of reactants within the reaction part of the microfluidic channel. In one embodiment, the reaction time within the reaction part of the microfluidic channel is calculated by taking the length of the reaction part of the microfluidic channel and dividing it by the flow rate of solution through the channel. In one embodiment, if the length of the channel is x and the flow rate is x/t, the reaction time t is t=x/(x/t).

In one embodiment, the height of the mixing part equals the height of the reaction part. In one embodiment, the width of the mixing part of the microfluidic channel varies between 10 μm and 150 μm along the length of this mixing part.

In one embodiment, the mixing part of the microfluidic channel is designed such that the direction of flow of liquid within the mixing part varies along the mixing part as depicted in FIG. 2a. In one embodiment, the direction of flow of liquid within the mixing part of the microfluidic channel is governed by the design of the mixing part of the channel. In one embodiment, the channel is constructed such that it forms a winding route to the liquid flowing within it. In one embodiment, the first part of the channel is twisted with respect to the straight line connecting the inlet and outlet of this first part. In one embodiment, portions of the mixing part of the channel are bent with respect to the virtual straight line stretching the inlet and outlet of this first part of the microfluidic channel In one embodiment, the length of the first part (the mixing part) of the microfluidic channel ranges between 0.15-3 mm. In one embodiment, the length of the first part of the microfluidic channel ranges between 0.1-1 mm. In one embodiment, the length of the first part of the microfluidic channel ranges between 1-2 mm. In one embodiment, the length of the first part of the microfluidic channel ranges between 1-3 mm.

In one embodiment, the length of the reaction part of the microfluidic channel ranges between 0.5 cm and 4 cm. In one embodiment, the length of the second part of the microfluidic channel ranges between 1.0 cm and 3.0 cm. In one embodiment, the length of the second part (the reaction part) of the microfluidic channel ranges between 0.5 cm and 1.5 cm. In one embodiment, the length of the second part of the microfluidic channel ranges between 2.0 cm and 6.0 cm. In one embodiment, the length of the second part of the microfluidic channel ranges between 0.1 cm and 2 cm. In one embodiment, the length of the second part of the microfluidic channel ranges between 1 cm and 10 cm. In one embodiment, the length of the second part of the microfluidic channel is 1 cm.

In one embodiment, the reaction time for mixed ingredients within the second part of the microfluidic channel is ranging between 5 ms and 60 ms. In one embodiment, the reaction time for mixed ingredients within the second part of the microfluidic channel is ranging between 1 ms and 100 ms. In one embodiment the reaction time for mixed ingredients within the second part of the microfluidic channel is ranging between 0.1 ms and 10 ms. In one embodiment, the reaction time for mixed ingredients within the second part (the reaction part) of the microfluidic channel is ranging between 1 ms and 1 s.

In one embodiment, the microfluidic device comprises a gas compartment. In one embodiment, the gas compartment is a gas chamber. In one embodiment, the gas compartment is surrounding at least a portion of the product outlet such that the gas compartment is coaxial with the product outlet.

In one embodiment, the gas compartment is attached to a gas inlet channel, and the gas compartment comprises a gas outlet proximal to a second end of the product outlet or proximal to the product outlet.

In one embodiment, the gas compartment is connected to a gas pressurized cylinder. In one embodiment, the gas cylinder is used to deliver gas through the gas inlet channel, through the gas compartment and out of the gas compartment. In one embodiment, the gas cylinder is further connected to a gas source such as a gas cylinder, a gas reservoir, a gas source chamber, a gas channel, a gas tube or a syringe.

In one embodiment, the gas delivered through the gas compartment comprises nitrogen ($N_2$). In one embodiment, the gas driven through the gas compartment comprises but is not limited to Ar, He, $CO_2$, air, water vapor. In one embodiment, the gas comprises a mixture of materials such as a mixture comprising two or more of the gases mentioned herein above.

In one embodiment, the flow rate of the gas through the gas compartment and out of the gas compartment is controlled. In one embodiment, the gas flow rate is controlled by a gauge connected to the gas pressurized cylinder. In one embodiment, the gas flow rate ranges between 1 m/s and 20 m/s. In one embodiment, the gas flow rate ranges between 5 m/s and 15 m/s. In one embodiment, the gas flow rate ranges between 7.5 m/s and 12.5 m/s. In one embodiment, the gas flow rate ranges between 0.1 m/s and 1 m/s. In one embodiment, the gas flow rate is about 10 m/s. In one embodiment, the gas flow rate ranges between 1 m/s and 100 m/s.

In one embodiment, the gas flow rate is higher than the liquid solution flow rate within the microfluidic channel. In one embodiment, the gas flow rate controls the ejection rate of the mixed and at least partially reacted material from the microfluidic channel. In one embodiment, the ejection rate depends on the gas flow rate and does not depend on the flow rate within the microfluidic channel. In another embodiment, the gas flow rate is lower than the liquid solution flow rate within the microfluidic channel. In another embodiment, the gas flow rate is equal to the liquid solution flow rate within the microfluidic channel In one embodiment, the gas compartment is of a rectangular shape. In one embodiment, the gas compartment is in the form of a cylinder. In one embodiment, the gas compartment is in the form of a ring. In one embodiment, the gas compartment is in the form of a tube. In one embodiment, the gas compartment has a conical shape.

In one embodiment, for a gas compartment of a rectangular shape, the width of the gas compartment ranges between 0.5 cm and 2 cm or between 1 cm and 3 cm or between 0.1 cm and 1 cm or between 1.5 cm and 2.5 cm or between 0.75 cm and 1.25 cm. In one embodiment, the width of the gas compartment is 1 cm.

In one embodiment, for a gas compartment of a rectangular shape, the length of the gas compartment ranges between 0.5 cm and 2 cm or between 1 cm and 3 cm or between 0.1 cm and 1 cm or between 1.5 cm and 2.5 cm or between 0.75 cm and 1.25 cm. In one embodiment, the length of the gas compartment is 1 cm.

In one embodiment, for a gas compartment of a rectangular shape, the depth of the gas compartment ranges between 1 mm and 3 mm; or between 0.5 mm and 1.5 mm; or between 0.75 mm and 1.25 mm; or between 0.1 mm and 0.5 mm; or between 0.5 mm and 10 mm; or between 1 mm and 3 mm. In one embodiment, the depth of the gas compartment is 0.5-2 mm.

In one embodiment, for a gas compartment of a cylindrical shape, the diameter of the gas compartment is of dimensions in the ranges described herein above for the length and width of the rectangular gas compartment.

In one embodiment, for a gas compartment of a cylindrical shape, the depth of the gas compartment is of the same dimensions as described herein above for the depth of a rectangular gas compartment.

In one embodiment, the gas compartment may acquire any other geometrical form as long as it surrounds at least a portion of the product outlet. According to this aspect, the gas compartment may be of a symmetrical, a non-symmetrical, or a partially-symmetrical form. The gas compartment may be elongated, round, of a cubical shape, triangular, oval, conical, disc-like or of any other shape. The gas compartment may comprise constant or varied dimensions such as constant or varied width, height, length, depth. In one embodiment, one part of the gas compartment is wider than another part. In one embodiment, the opening of the gas compartment is narrower than the inner part of the gas compartment. In one embodiment, the gas compartment gets narrower toward its outlet. In one embodiment, at the outlet of the gas compartment, the opening of the gas compartment is a circular hole of a diameter of 2 mm, while the cross section of the inner part of the gas compartment that is embedded in the first substrate is a 1 cm×1 cm wide square. In one embodiment, such configuration is achieved by placing a glass slide with a 2 mm diameter hole on top of the 1 cm×1 cm square hole comprising a portion of the gas compartment, such that the opening of the gas compartment (the gas outlet) acquires the smaller dimensions of the hole in the glass slide. In one embodiment, such configuration results in efficient gas flow out of the gas compartment. One embodiment of a microfluidic device is described in Example 1.

In one embodiment, the gas compartment surrounds the product outlet. In one embodiment, the product outlet is in the form of a channel, a cylinder, a hose, or a tube. In one embodiment, the product outlet protrudes from the gas compartment. In one embodiment, when product is ejected from the product outlet, the product is surrounded by flow of gas that is ejected from the gas container (compartment). In one embodiment, the gas flow around the product outlet provides gas sheath flow around the product coming out of the product outlet channel. In one embodiment, the direction of the gas flow ejected from the gas compartment is parallel to the direction of the product flow out of the product outlet.

In one embodiment, the gas inlet channel is cylindrical. In one embodiment, the gas inlet channel has a diameter of 1 mm. In one embodiment, the diameter of the gas inlet channel is ranging between 0.1 mm and 5 mm. In one embodiment, the length of the gas inlet channel is ranging between 1 cm and 5 cm. In one embodiment, the length of the gas inlet channel is ranging between 0.5 cm and 2.5 cm.

In one embodiment, the microfluidic device comprises a first substrate. In one embodiment, the microfluidic channel, the inlets, the gas channel or a combination thereof are embedded in this first substrate.

In one embodiment, the first substrate comprises an organic material. In one embodiment, the first substrate comprises inorganic material. In one embodiment, the first substrate comprises a polymer. In one embodiment, the first substrate comprises polydimethylsiloxane (PDMS). In one embodiment, the first substrate comprises metal and/or $SiO_2$.

In one embodiment, the width, length or a combination thereof of the first substrate ranges between 1 cm and 10 cm. In one embodiment, the width, length or a combination thereof of the first substrate ranges between 1 cm and 5 cm. In one embodiment, the width, length or a combination thereof of the first substrate ranges between 2 cm and 8 cm. In one embodiment, the width of the first substrate is 2.5 cm and the length of the first substrate is 5 cm. In one embodiment, the width, length or a combination thereof of the first substrate ranges between 3 cm and 6 cm.

In one embodiment, the microfluidic device comprises a second substrate such that the second substrate is in contact with the first substrate and in contact with the microfluidic channel, the inlet channels, or a combination thereof.

In one embodiment, the second substrate covers the microfluidic channels thus defining the height (depth) of the channels. By covering the first substrate comprising the channels with the second substrate, the liquid solution transferred through these channels is confined to the channels. An embodiment of the second substrate is depicted in FIG. 1d (2). The second substrate (#2 in the figure) is attached to the first substrate, thus sealing the channels from below. (FIG. 1d is a cross section of the microfluidic device showing the microfluidic channel (light gray) that is attached to the first substrate above and to the second substrate (#2) below).

In one embodiment, the second substrate comprises glass. In one embodiment, the second substrate comprises silicon dioxide, silicon nitride, quartz, SU-8 or a combination thereof. In one embodiment, the second substrate is transparent and in another embodiment, it is opaque. In one embodiment, the second substrate comprises inorganic material, organic material or a combination thereof. In one embodiment, the second substrate comprises, metal, metal alloy, ceramic, polymer, plastic, oxide. In one embodiment the surface of the second substrate that is in contact with the microfluidic channels and optionally with the inlet channels is coated. In one embodiment, the coating is by a material that is inert to reaction with the mixed materials and solutions that flow within the microfluidic channels.

In one embodiment, the width, length or a combination thereof of the second substrate are as described herein above for the width and length of the first substrate.

In one embodiment, this invention provides an apparatus for sample preparation, the apparatus comprising:
  a microfluidic device comprising:
    a microfluidic channel comprising a first mixing part and a second reaction part, wherein said channel further comprises a first inlet and a second inlet;
    a product outlet, wherein said product outlet is attached to said microfluidic channel;
    a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;
  wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet.
  materials from said product outlet;
  a cooling device comprising:
    a translation element comprising a surface; and
    a cooling means;
  wherein said translation element is cooled by said cooling means;

wherein said product outlet of said microfluidic device is placed in proximity to said cooling device such that material can be transferred from said microfluidic device onto different areas on said surface of said translation element.

In one embodiment, the cooling device is needed in order to freeze and keep the samples ejected from the microfluidic device frozen. In one embodiment, the cooling device is needed in order to keep the samples ejected from the microfluidic device at a low temperature. Freezing the samples or keeping it at low temperature is required in order to stop or inhibit further reaction between the reactants in the sample. This is crucial when studying the kinetics of a reaction and when samples are collected for different reaction times. When the sample is frozen, it should be kept frozen with no further reaction until it is being measured, inspected or examined for sample content.

In one embodiment, the translation of the novel cooling device of this invention is important for ejecting subsequent sample drops (or subsequent droplet collections) on different locations on the surface of the translation element. If two subsequent drops would be dropped one on top of the other, the second drop may not freeze immediately as the first drop is not as cold as the translation element's surface. By moving the surface of the translation element, subsequent sample drops will fall directly on the surface of the element and will freeze immediately, thus halting any further reaction.

In one embodiment, the translation of the novel cooling device of this invention is important for being able to collect samples of various reaction times on different areas on the surface of the translation element. According to this aspect and in one embodiment, the injection rate of reactant solution into the microfluidic device is set, and after some time, sample of reacted material solution (mixed solution) is ejected from the microfluidic device onto a certain area on the cooling device. During ejection of one sample, sample drops (or collections of small sample droplets) may be placed adjacent to each other as the cooling device rotates as explained herein above. Once the amount of sample needed is accumulated on the cooling device, ejection from the microfluidic device may be either stopped or continued. The translation element is then translated to a different area. The rate of injection of a sample into the microfluidic device is then changed such that the reaction time within the microfluidic device changes as well. The sample corresponding to the new reaction time is applied to a different area of the surface of the cooling element as the cooling element rotates. Accordingly, samples of different reaction times can be collected serially on the same surface but on different locations. This procedure is very efficient and it requires only one experiment for the collection of all samples needed. In one embodiment, the translation element translates continuously while the samples are ejected continuously from the device. During this continuous motion the flow rate within the microfluidic channel is changed and as a result, samples corresponding to different reaction times are collected on different areas on the surface of the translation element.

In one embodiment, the distance between the surface of the translation element and the second end of the product outlet, ranges between 2.5 mm and 7.5 mm In one embodiment, the sample solution when ejected from the product outlet is mixed with gas ejected from the gas outlet and the sample forms small droplets. In one embodiment, the sample solution when ejected from the product outlet channel is mixed with gas ejected from the gas outlet and an aerosol is formed. The aerosol comprises very small drops of sample solution. The formation of small solution drops is advantageous for numerous reasons. First, small drops freeze more rapidly on the surface of the cooling device, thus preventing further reaction within the sample solution. Second, frozen small drops are much easier to collect from the surface of the translation element into capillaries. This is in contrast to large frozen drops that need to be grounded first in order to be inserted into a capillary.

In one embodiment, this invention provides novel devices and methods that utilize gas for the formation of aerosol and/or for the formation of small droplets such that the aerosol/small droplets comprise the sample solution ejected from a microfluidic device. The formation of an aerosol or the formation of small sample droplets which is enabled by mixing the ejected solution drops with the gas sheath flow allows ejection of the solution drops from the product outlet. When gas sheath flow is not used, the sample ejected from the product outlet channel remains attached to the product outlet (outlet channel) as a drop and cannot be transferred to the cooling device in one embodiment.

In one embodiment, the application of gas sheath flow around the liquid sample ejected from the product outlet of the microfluidic device enables faster ejection and faster freezing of the ejected sample. According to this aspect and in one embodiment, the gas flow rate is much higher than the sample flow rate and therefore, the ejected sample acquires the higher gas flow rate and is being collected much faster on the surface of the cooling device. This feature enables to achieve much higher accuracy in reaction times. It also provides control over the sample content as the time between ejection from the microfluidic device and freezing on the cooling surface is very short.

In one embodiment, the translation element is motorized. In one embodiment, translation element is movable around an axis, along an axis or a combination thereof. In one embodiment, the motor is used to move, to translate, to rotate, to change position of, to change position of, and/or to relocate the translation element.

In one embodiment, the translation element comprises a stage. In one embodiment, the translation element comprising a belt.

In one embodiment, the cooling means comprises contacting said translation element with liquid nitrogen. In one embodiment, the bottom area of the translation stage is cooled by liquid nitrogen. In one embodiment, the bottom area of the belt is cooled by liquid nitrogen.

In one embodiment, the translation stage is conical in shape such that the top surface of the translation stage is in the form of a circle, and the bottom conical area of the stage (which is smaller in diameter than the top surface) is cooled by liquid nitrogen.

In one embodiment, the apparatus is encapsulated in or surrounded by a box filled with nitrogen gas. In one embodiment, the nitrogen gas environment reduces humidity around the samples ejected from the microfluidic device. In one embodiment, reduced humidity aids in preserving the samples. In one embodiment, nitrogen atmosphere inhibits or prevents sample deterioration. In one embodiment, $N_2$ atmosphere keeps the samples from undergoing undesired reactions when ejected from the microfluidic device. In one embodiment, any other inert gas can be used instead of nitrogen in the box surrounding the apparatus of the invention. In one embodiment, Ar is used as the gas filling the box. In one embodiment, the pressure of the gas inside the box is atmospheric pressure. In another embodiment, the pressure of the gas inside the box is higher than atmospheric pressure or is lower than atmospheric pressure.

In one embodiment this invention provides a sample collection system comprising:
  a translation element comprising a surface; and
  a cooling means;
wherein said translation element is cooled by the cooling means;
and wherein the sample collection system is placed in proximity to a sample production system such that material can be transferred from the sample production system onto different areas on the surface of the translation element of the sample collection system.

In one embodiment, the sample collection system enables rapid freezing of the sample collected on it. In one embodiment, the sample collection system enables serial collection of samples on different areas on the surface of the sample collection system. According to this aspect and in one embodiment, the translation element is being moved while different samples are collected on it such that different samples are collected on different areas on the surface of the translation element. In one embodiment, the movement of the translation element is continuous. In one embodiment the translation element is moved only after one sample was collected on it and it stops moving before another sample is collected on it. In one embodiment, translation of the translation element allows rapid freezing of various sample drops on the cooled surface of the translation element.

In one embodiment, the translation element is cooled by the cooling means to a liquid nitrogen temperature or to a temperature slightly higher than liquid nitrogen temperature. In one embodiment, the surface of the translation element is cooled to a temperature below zero degrees Celsius. In one embodiment, the surface of the translation element is cooled to a temperature ranging between 0 and (−100) degrees Celsius. In one embodiment, the surface of the translation element is cooled to a temperature ranging between 0 and (−10) degrees Celsius or to a temperature ranging between 0 and (−20) degrees Celsius or to a temperature ranging between 0 and (−50) degrees Celsius.

In one embodiment, such collection system can be coupled to any sample preparation system. In one embodiment, such sample collection system allows collection of many samples from one experiment or from one batch. In one embodiment, such collection system allows efficient performance of biological assays. In one embodiment, such collection system allows efficient sample collection for kinetics/reaction mechanism studies. In one embodiment, such collection system is used for diagnostics. In one embodiment, such collection system is used for drug development.

Methods of the Invention

In one embodiment, this invention provides methods for mixing materials, methods for cooling materials and methods of sample preparation for analysis. In one embodiment, this invention provides a method for mixing small volumes of reactants for generating a chemical or biological reaction. In one embodiment, this invention provides methods for mixing chemical/biological reactants, and collecting the resultant materials. In one embodiment the chemical/biological materials or reactants are part of a solution. In one embodiment, the solution is aqueous. In one embodiment, the solution is organic. In one embodiment, the solutions comprising the reactants are mixed according to methods of this invention and the reactants get into contact and react. In one embodiment after a certain period of time, the mixed solutions comprise reactants and product or products of a chemical or biological reaction that occurred upon mixing of the reactants. In one embodiment, products of certain reactions are intermediates.

In one embodiment, a product of a reaction that occurred during a certain time period serves as a reactant for a reaction that follows. In one embodiment, a complete reaction comprises reaction steps in which certain reactants are consumed and certain products are formed. In one embodiment, methods of this invention provide means for collecting the mixed solutions after various periods of time. In one embodiment the collected samples are rapidly frozen in order to stop further chemical or biological reaction.

In one embodiment, this invention provides a method of preparation of samples for analysis, said method comprising:
a. providing an apparatus for analysis, said apparatus comprising:
  a microfluidic device comprising:
    a microfluidic channel comprising a first mixing part and a second reaction part, wherein said channel further comprises a first inlet and a second inlet;
    a product outlet, wherein said product outlet is attached to said microfluidic channel;
    a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;
  wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet;
  a cooling device comprising:
    a translation element comprising a surface; and
    a cooling means;
  wherein said translation element is cooled by said cooling means;
  wherein said product outlet of said microfluidic device is placed in proximity to said cooling device such that material can be transferred from said microfluidic device onto different areas on said surface of said translation element.
b. cooling said translation element using said cooling means;
c. translating said surface of said translation element such that said top surface of said translation element remains at a constant vertical distance from said microfluidic device;
d. injecting a first reactant solution from said first inlet and a second reactant solution from said second inlet such that said first reactant and said second reactant get into contact at said mixing part and wherein said reactants are mixed within said mixing part and wherein said reactants at least partially react within said reaction part;
e. ejecting samples comprising at least partially reacted materials in a serial manner from said product outlet onto different areas of said surface of said translation element, wherein upon ejecting, the product solution is mixed with gas ejected from said gas compartment thus facilitating ejection of said product solution.

In one embodiment, injecting a first reactant solution from said first inlet and a second reactant solution from said second inlet is conducted using an injection pump.

In one embodiment, the reaction time of the reactants is controlled by the injection rate of the injection pump.

In one embodiment, the reaction time is in the millisecond (ms) range.

In one embodiment, the number of samples transferred from the microfluidic device to the translation stage ranges between 1 and 100.

In one embodiment, the microfluidic device is connected to a motor. In one embodiment, the microfluidic device is moved horizontally with respect to said surface of said translation element. In one embodiment, by horizontally moving said microfluidic device with respect to the surface of the translation element, the samples are transferred to different areas on the surface of the translation element.

In one embodiment, the different samples ejected from the microfluidic device following different reaction times are serially collected on different areas of the surface of said translation element. In one embodiment, samples of different reaction times freeze on a different radius of a rotating circular plate, thus enabling a higher rotation speed. This is achieved by rotating the cooled plate and by horizontally moving the microfluidic device with respect to the surface of the cold rotating plate, such that when the reaction time changes, the sample is ejected onto a different radius on the rotating plate. Such configuration also facilitates automatic transfer of the samples into a set of capillaries that are assembled in a row and span the radius of the cold plate. The capillary set may be brought into contact or to close proximity with the surface of the cold plate such that each capillary collects a sample from a different radius of the plate. Accordingly, each capillary collects a sample of different reaction time.

In one embodiment, the reaction time is controlled by injection flow rate. In one embodiment, the sample ejected from the microfluidic device, is mixed with the gas ejected from the gas outlet to form an aerosol or to form small droplets. In one embodiment, the aerosol/small droplets sample freezes upon contact with the surface of said cooling element. In one embodiment, the sample freezes in small drops on the surface of the cooling element. In one embodiment, the diameter of the drops ranges between 0.05 mm and 1 mm. In one embodiment, the diameter of the drops ranges between 0.01 mm and 0.1 mm. In one embodiment, the diameter of the drops ranges between 0.05 mm and 0.5 mm. In one embodiment, the diameter of the drops ranges between 0.1 mm and 1 mm In one embodiment, following sample transferring onto the surface of the translation element, the samples are transferred to capillaries. In one embodiment, transferring into capillaries is automated. In one embodiment, transfer into capillaries is manual. In one embodiment, all samples are transferred at the same time into a set of capillaries. In one embodiment, the samples are transferred serially into the capillaries. In one embodiment, following transfer of samples to the capillaries, the capillaries are frozen in liquid nitrogen. In one embodiment during transfer the capillaries are maintained at a low temperature. In one embodiment, during transfer the capillaries are maintained at a temperature of below zero degrees Celsius (below 0° C.).

In one embodiment, the capillaries are transferred to an analysis instrument. In one embodiment, the analysis instrument comprises an optical spectrophotometer, a mass spectrometer, an NMR instrument, an instrument for magnetic analysis, an electrical properties analysis instrument, a surface analysis instrument, a microscope, a chromatography tool, an electrophoresis set up or a combination thereof. In one embodiment, the analysis instrument is electron paramagnetic resonance (EPR) instrument.

In one embodiment, the method is used to study kinetics of reactions.

Definitions:

In one embodiment, aerosols of this invention are suspensions of liquid particles in a gas. The aerosol includes both the particles and the suspending gas. The concentration of the aerosol may be measured as mass concentration defined as the mass of particulate matter per unit volume with units such as $\mu g/m^3$. It can also be measured as Number concentration, the number of particles per unit volume. In one embodiment, the liquid particles are drops or droplets.

In one embodiment, the "microfluidic device" is a device wherein fluid flows through channels or conduits that have a cross section with diameter or width/depth in the micrometer range. For example, a microfluidic device comprises channels or conduits defined in a substrate wherein the width and depth of the channels/conduits ranges between 10 micrometer ($\mu m$) and 500 micrometer. In another embodiment, the microfluidic device comprises microfluidic channels (channels comprising width and/or depth or diameter in the micrometer range) that are not defined in a substrate but rather are bonded to a substrate. In another embodiment, the microfluidic channels are not fixed to a substrate.

In one embodiment, the term "mixer" is used to describe the microfluidic device. In another embodiment, the term "mixer" describes only the first portion, i.e. the mixing portion or the mixing part of the microfluidic channel where mixing of the incoming reactants occur. In one embodiment, this first portion of the microfluidic channel is designed to provide efficient mixing by changing the dimensions of the channel and by changing the flow direction of the solution through the "mixer" channel. In one embodiment, when reactants exit the "mixer" part of the microfluidic channel the reactants are thoroughly mixed.

In one embodiment, "mixing time" refers to the time the reactant solutions spend within the mixing part of the microfluidic channel. In one embodiment, mixing time is the time period starting when the first and second materials enter the mixing part and ending when the first and second materials (and any products of their reaction) exit the mixing part. In one embodiment, the mixing time is negligible when compared with the reaction time. In one embodiment, the mixing time is in the microseconds range.

In one embodiment, "reaction time" refers to the time the reactants spend in the reaction part of the microfluidic channel. In one embodiment, the reaction time is the time it takes for the reactants entering the reaction part to reach the end of the reaction part. In one embodiment, the reaction time is calculated by dividing the length of the reaction part by the flow rate within the reaction part of the microfluidic channel.

In one embodiment, the deadtime is the shortest reaction time that can be accessed with the RFQ device. In one embodiment, a deadtime of 5 ms means that samples with reaction times shorter than 5 ms cannot be accurately collected or measured. In one embodiment, a deadtime of 5 ms means that only samples with reaction times of 5 ms or more can be collected in devices and methods of this invention. In one embodiment, a deadtime of 5 ms means that only time points of 5 ms or more can be collected in devices and methods of this invention.

In one embodiment, in devices of this invention, a first material is introduced from a first inlet and a second material is introduced from a second inlet into the mixer. In one embodiment, the first and second materials comprising solutions. In one embodiment, the solutions comprise a solvent and at least one solute. In one embodiment, the solvent is water and the solution is an aqueous solution. In one embodiment, the solutes comprise atoms, ions, molecules, clusters, aggregates, nanoparticles or a combination thereof. In one embodiment, the molecules are biological molecules. In one embodiment the molecules comprises enzymes, substrates, polymers, oligomers, amino acids, proteins, DNA, RNA, or a combination thereof. In one embodiment, the solutions comprising biological cells or cell components. In one embodiment, the solutions comprising non-biological molecules. In one embodiment, the solutions comprise reactants for chemical reactions. In one embodiment, the solvent is organic and the solutions are non-aqueous.

In one embodiment, one reactant is introduced from one inlet and a series of other reactants is introduced from another inlet. In one embodiment, a series of reactions for a certain reactant can be measured in devices of this invention. According to this aspect and in one embodiment, one reactant is introduced from a first inlet while a series of other reactants is serially introduced from a second inlet. The products of the resulting series of reactions are collected on different areas of the translation element. According to this aspect and in one embodiment, devices and methods of this invention are used for biological assays and for diagnostics.

In one embodiment, more than two inlets are used. According to this aspect and in one embodiment, one reactant can be introduced to the mixer through at least two inlets, and a second reactant is introduced to the mixer through at least two other inlets. In one embodiment, efficient mixing can be achieved using multiple inlets for each reactant.

In one embodiment the terms reactant, reactant solution, material(s), species of interest, ingredient, fluid solution, liquid solution, product, product solution are used to describe the materials, solutions, mixes and compounds and samples introduced into and/or ejected from microfluidic devices of the invention. In one embodiment, the samples ejected from the microfluidic device and collected on the translation element comprise reactant(s), reactant solution, solvent, products, intermediates, other materials, species of interest, solution ingredient, solutes, stabilizers, buffers, fluids, liquids, or a combination thereof. In one embodiment, a "sample" comprises droplet(s) of the solution that is ejected from the product outlet of the microfluidic device. In one embodiment, the "sample" comprises the solution and the solution content.

In one embodiment, at least a portion of the materials react within the reaction part of the microfluidic channel. In one embodiment, the material reacted forms products of reaction. In one embodiment, these products are reactants in further reactions that occur within the reaction channel. In one embodiment, intermediates are formed as the results of reactions that take place within the reaction part. In one embodiment, the amount of intermediates or products formed within the reaction part is above the detection limit of the analysis instrument and is detected. In one embodiment, the amount of intermediates or products formed is below the detection limit of the analysis instrument used. In one embodiment, reaction may start within the mixing part of the microfluidic channel. In one embodiment, since the mixing time is negligible when compared with the reaction time, such reaction does not affect the accuracy of the measurement of the reaction mechanism studied.

In one embodiment, the term "a" or "one" or "an" refers to at least one. In one embodiment the phrase "two or more" may be of any denomination, which will suit a particular purpose. In one embodiment, "about" or "approximately" or "roughly" may comprise a deviance from the indicated term of +1%, or in some embodiments, −1%, or in some embodiments, ±2.5%, or in some embodiments, ±5%, or in some embodiments, ±7.5%, or in some embodiments, ±10%, or in some embodiments, ±15%, or in some embodiments, ±20%, or in some embodiments, ±25%.

The following examples are presented in order to more fully illustrate the preferred embodiments of the invention. They should in no way be construed, however, as limiting the broad scope of the invention.

EXAMPLES

Example 1

Fabrication of the Microfluidics Device

The sample mixer and channels were designed using AutoCAD (Autodesk) and printed on masks (laser plotter Suron). The preparation of the mixer consists of three steps: (i) fabrication of the master pattern, (ii) fabrication of the PDMS (polydimethylsiloxane) stamp and (iii) attachment of the PDMS stamp to glass slides. These steps are described in details next.

(i). Fabrication of the master pattern. The master pattern (FIG. 1a 2) was fabricated using the following standard soft lithography procedure. A 2" diameter silicon wafer was cleaned thoroughly with acetone, isopropanol and water, dried with nitrogen gas and then placed on a hot plate at 150'C for 20 min. The cleaned wafer was then covered with a 50 μm layer of SU-8 3050 photoresist (Microchem, cat: MCC-SU8-3050-500), using a spin coater set to 3000 rpm and 30 sec. The wafer was placed on a hot plate (95° C.) for 10 min. The covered wafer and a photo-mask, patterned with the desired channels and mixer structures, were loaded onto a mask-aligner, aligned and exposed to UV light. The exposed wafer was then post-baked on a hot plate for 1 min at 65'C and 5 min at 95'C. After equilibration at room temperature for 5 min the wafer was developed with a PM-Acetate (1-Methoxy-2-propyl acetate) developer, washed with isopropanol and water, and stored in a clean Petri-dish.

(ii) Fabrication of the PDMS stamp. A 10:1 (w/w) base and curing agents of Sylgard 184 silicone elastomer (Dow corning 184 Sylgard elastomer 0.5 KG kit) were mixed thoroughly in a plastic cup and poured on the master pattern (FIG. 1a2) that was placed in a Petri-dish lid. The filled Petri-dish was transferred to a desiccator for two hours to remove air bubbles. A 2×2 $cm^2$ microscope slide with a 1×1 $cm^2$ embossed rectangle (FIG. 1a1) was placed upside-down on the filled lid, with its centered aligned with end of the channel in the master-pattern, and 5 mm above it (below is the liquid PDMS). The whole setup (FIG. 1b) was placed for 4 h in an oven at 80° C. to cure the PDMS prepolymer. The cured PDMS stamp was then separated from the slide, lid and wafer (FIG. 1c), and pierced with a 14 gauge needle (McMaster-Carr 75165A672) at the inlet positions of the two reacting solutions, and at the $N_2$ gas inlet, located close to the outlet of the reaction mixture. The PDMS stamp was cleaned with soap and water and dried.

(iii) Attachment of the PDMS stamp to glass slides. Covering the device was conducted as follows: A 2.5×5.0 $cm^2$ microscope glass slide (FIG. 1d2), and a 2×2 $cm^2$ glass with 2 mm diameter hole at the center (FIG. 1d1) were cleaned thoroughly with acetone, soap, and water and dried.

The glass slides and the PDMS stamp were then placed in oxygen plasma cleaner for oxidation at 150 mtorr of oxygen, 150 mtorr of argon and 150 W of radio frequency for 1 min. This surface treatment allows attachment of these parts without the use of adhesives. The smaller glass was attached to the PDMS side of the mixture output with its center aligned with the end of the output channel, producing a small chamber above it. This assembly (FIG. 1d) was incubated at 80° C. for 1 h to strengthen the seal. Two Tygon tubing (i.d. 0.38 mm, o.d. 2.31 mm, Cole-Panner 0574-95609-14) were introduced into the inlet holes. The other ends of the tubes were connected to a 22 Gauge blunt syringe needle (McMaster-Carr75165A682), coupling the syringes and syringe pump to the microfluidic device (FIG. 1e). The pump used was a "HARVARD-apparatus 11plus, two syringe model".

FIG. 1 is a description of the fabrication of a microfluidic device. (a) PDMS solution was placed between the patterned silicon wafer (a2) and the patterned cover glass (a1) and cured. (b) a side view of the assembly after curing. (c) removal of the patterned silicon wafer and the patterned glass after curing. (d) a clean glass base (d2) and a cover upper glass with a hole (d1) were attached to the patterned PDMS using plasma to produce closed channels. (e) The outlet nozzle and tubes were connected to the final device.

Mixing of solutions in the microfluidic device was tested using two non-fluorescent solutions, which turn fluorescent upon mixing. One syringe contained 0.05 mM solution Fluorescein (excitation at 494 nm and emission at 521 nm), 5 μM DMSO, 0.1% Tween and 5 mM acetic acid, pH 3.5, and the second contained 50 mM Tris-HClpH 8.8. Fluorescein has a pKa of 6.4 and it fluoresces only when the pH is 5-9. After mixing the pH became basic and the Fluorescein fluorescence was measured. The device was placed under a microscope (Axiovert 25 Zeiss,) with a ×20 objective magnification (ph2 Achrostigmat x20/0.45) and a mercury vaporshort-arc lamp (HBO-100). A test area, immediately after the mixer, was photographed by a CCD camera (AN-DOR Luca EMCCD) and the density of pixels per unit area, which is proportional to the fluorescence intensity, was determined.

Figure 6:
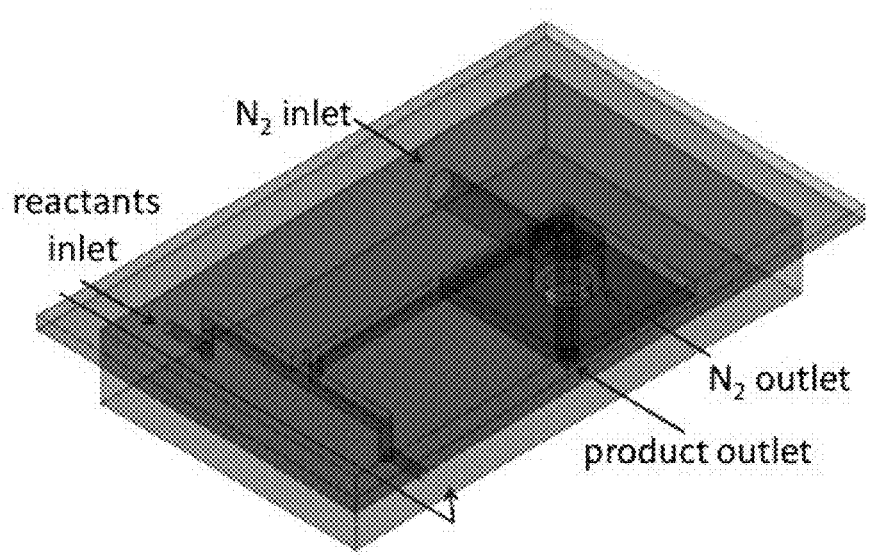
FIG. 6 is a close-up of a microfluidic device.

FIG. 6 is a close-up of the microfluidic device. The device consists of 20×50 mm² microscope glass (top) attached to a PDMS (polydimethylsiloxane) rubber (bottom). A "T" shape channel with diameter of 50 μm is minted in the PDMS next to the glass. Each one of the short arms of the "T" is about 10 mm and is connected to an inlet tube from which the reactants enter the device. At the junction of the "T" shape channels there is a mixer pattern which mixes the two reactants. The reaction occurs in the long arm of the "T" shape channels, which is about 25 mm long. At the end of this channel and perpendicular to it, there is a needle from which the product is sprayed out of the device. In the PDMS around the outlet needle there is a chamber for nitrogen gas. The gas enters from the side of the device and flows out around the needle while pushing the product out from the needle end.

Example 2

EPR Measurements

The test reaction was reduction of the nitroxide free radical, TEMPOL, (4-hydroxy-2,2,6,6-tetramethyl-piperidine 1-oxyl (Aldrich, cat: 17614-1)), by sodium dithionite (Aldrich), using $Mn^{+2}$ as an internal standard. The two solutions mixed were: (1) TEMPOL 0.5 mM, $MnCl_2$ 1 mM and (2) sodium dithionite 100 mM. Both in 15 mM phosphate buffer, pH 7.0, 30% v/v glycerol/water [14].

The EPR measurements were carried out on a home build pulsed W-band spectrometer. Samples were collected into capillaries of 0.8 mm o.d., 0.64 mm i.d., and length of 10 mm out of which ~2 mm are in the active area of the cavity. Echo-detected (ED) EPR spectra were recorded at 25K using the two-pulse echo sequence. Since TEMPOL (S=1/2) and $Mn^{+2}$ (S=5/2) differ in their nutation frequencies and spin-lattice relaxation times, $T_1$, the optimal conditions for detecting both were pulses of 50, 100 ns with an inter-pulse delay τ=550 ns and a repetition time of 5 ms. The power was adjusted such that the $Mn^{2+}$ echo intensity at the lowest field hyperfine component and the nitroxide echo intensity at a field corresponding to its max intensity were comparable.

Example 3

Operation of an RFQ Microfluidic System

Figure 2:
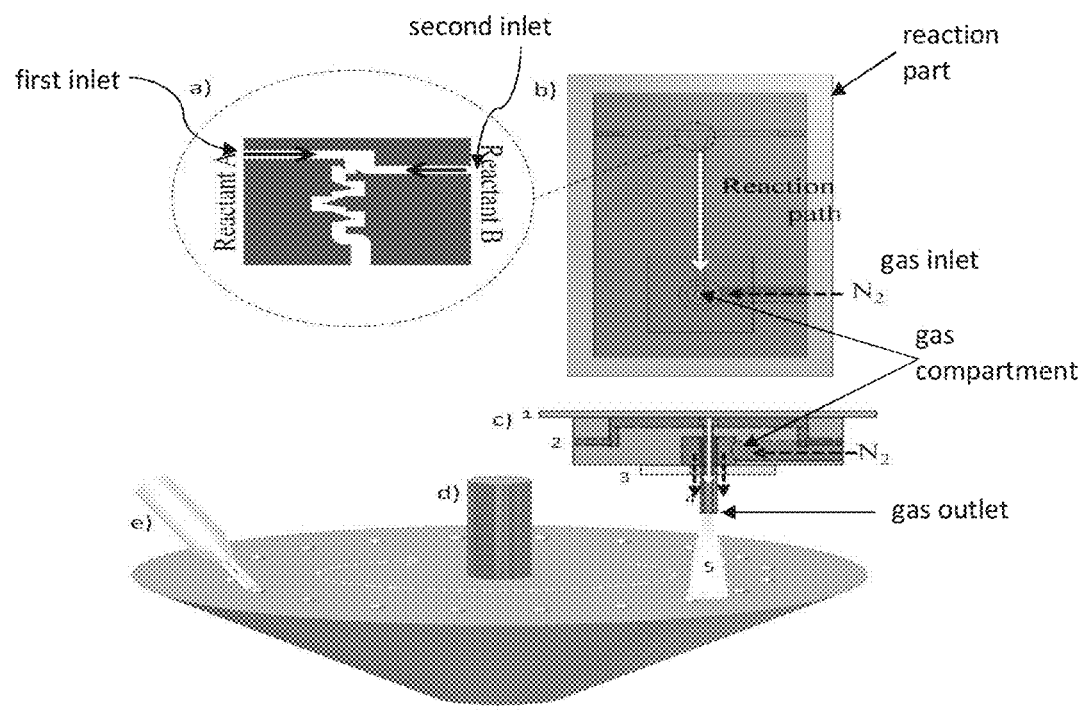
FIG. 2 illustrates an embodiment of an RFQ apparatus; the mixer (a); the reaction path in the device (b); spraying the mixture out of the device (c); freezing on a rotating metal disk (d); and collection into capillaries (e). (a) and (b) are top views of the microfluidic device while (c) is a side view of the microfluidic device.
Figure 7:
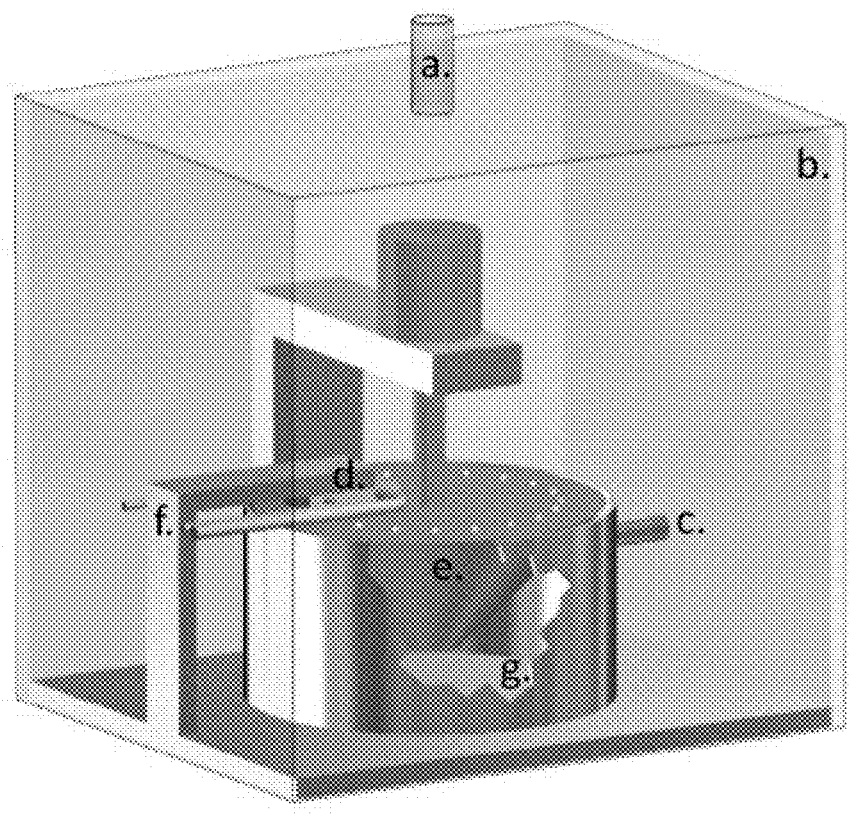
FIG. 7 is a schematic illustration of the RFQ apparatus. (a) a gas inlet channel, optionally connected to a pressurized gas cylinder; (b) a gas compartment; (c) means for cooling refill inlet; (d) reaction part of the microfluidic channel; (e) a cooling device; (f) first and second reactant inlets, optionally connected to an injection pump; and (g) means for cooling.

A microfluidic apparatus was assembled as follows. The RFQ microfluidic apparatus comprised two main parts: the microfluidic device and the freeze-quench setup. The microfluidic device comprises a mixer, which mixes the two reacting solutions, a flow path where the reaction occurs, and a sprinkler from which the solution is sprayed out of the device (FIG. 2 a,b,c and FIG. 6). This device was connected to a dual syringe pump, which injects the reactants, and to a nitrogen gas source, which pushes the products out of the device. The freeze-quench setup consisted of an aluminum rotating plate on which the mixed solution freezes. This plate was placed in a liquid nitrogen bath, such that the liquid nitrogen comes in contact with the bottom of the plate and cools it (FIG. 2d). The whole setup was placed in a nitrogen gas box to isolate the system from the surrounding moisture (see FIG. 7). FIG. 7 is a schematic illustration of the whole RFQ apparatus. It consists of a microfluidic device where the reaction occurs (d), the freezing part where the sample freezes (e) and later on collected from, and a box (b) which is filed with nitrogen, introduced from and through inlet (a), to prevent the accumulation of humidity. The reactants and nitrogen gas enters the microfluidic device (f), are mixed, react and sprayed out onto the freezing rotating plate (e). The plate is cooled down by liquid nitrogen in the chamber (g) refilled through (c).

Figure 8:
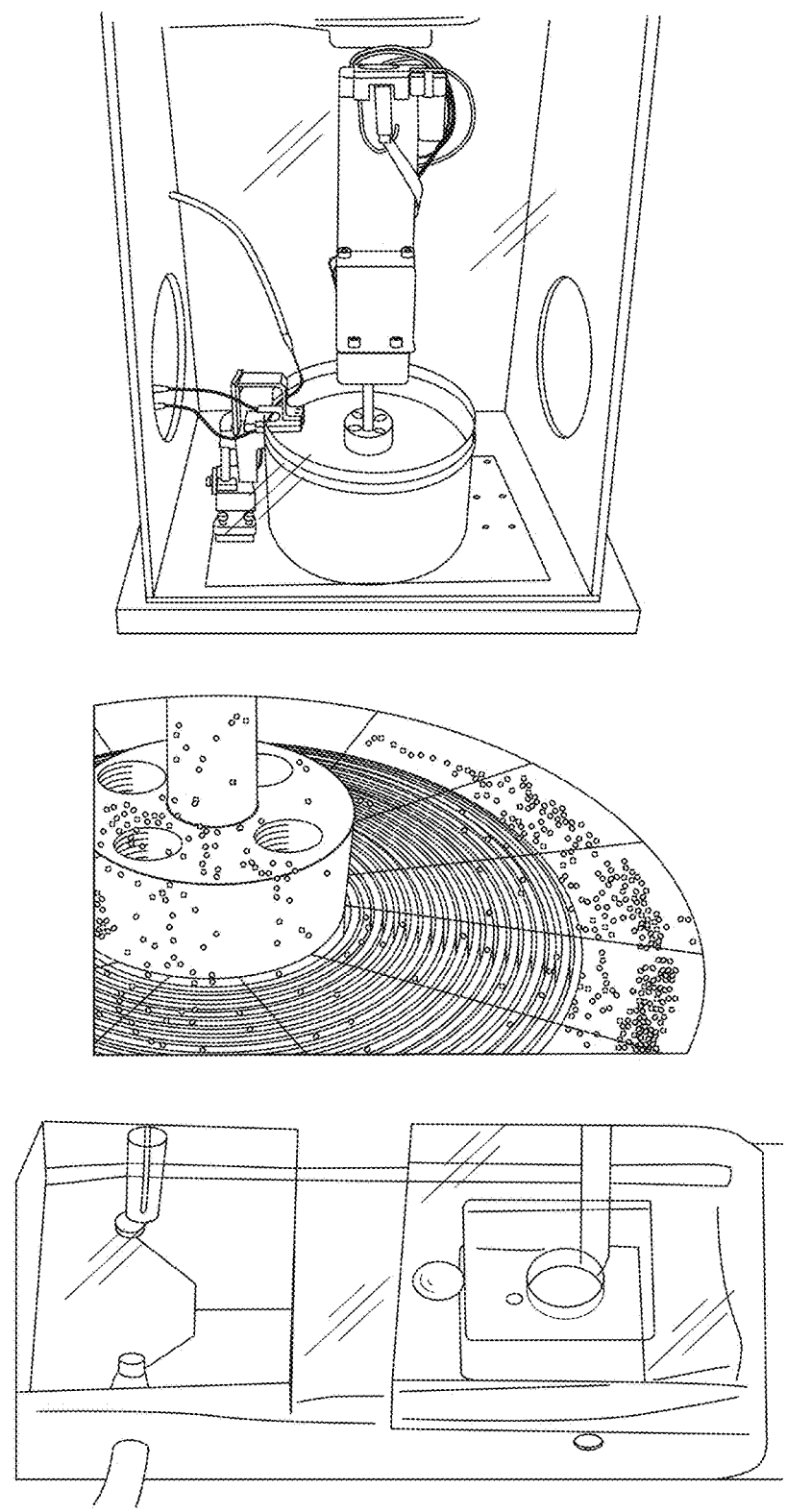
FIG. 8 shows images of one embodiment of a device. Top: a picture of the RFQ apparatus; center: an image of the collection plate; and bottom: the microfluidic device.

FIG. 8 shows images of one embodiment of an apparatus of this invention. Top: a picture of the RFQ apparatus; center: an image of the collection plate (translation element) at the end of the reaction wherein the white radius lines show the locations of the samples with different reaction times; and bottom: the microfluidic device.

FIG. 2 illustrates an embodiment of an RFQ apparatus. Reactants A and B enter the mixer (a), are mixed and the reaction begins. The reaction occurs along the channel coming out of the mixer (b, white arrow). The reaction time at the end of this channel is determined by the flow speed and the channel length. The mixture is then sprayed out of the device (c5) with nitrogen gas sheath flow (c4) and freezes on a rotating metal disk, immersed in liquid $N_2$ (d). The frozen sample is then rapidly collected into capillaries (e) that are then dumped into liquid $N_2$. The microfluidic device consists of glass base (c1), a PDMS body that contains the mixer and channels (c2), and a cover glass with a nozzle outlet (c3).

Mixing.

The mixing of fluids flowing through a pipe can be characterized by a Reynolds number (Re) that is the ratio of the inertial (v·ρ) and viscous forces (μ/d):

$$Re = \rho \cdot v \cdot d/\mu \quad (1)$$

In eq. (1) ρ, μ, v, and d, are the density, viscosity, linear flow rate of the fluid, and pipe diameter, respectively. For aqueous solutions in microfluidic channels: $\rho = 1$ g/cm$^3$, $\mu = 0.01$ g/cm·s, v=1 cm/s–1 m/s and d≈50 μm. These yield Re=1-100. Under conditions of low Re (Re<2000) the flow in the pipe is laminar and mixing is achieved by diffusion. The diffusion time ($\tau_D$) is given by:

$$\tau_D = \delta^2/D \quad (2)$$

where δ and D are the diffusion length and diffusion coefficient, respectively. For small molecules in aqueous solutions D ~$10^{-9}$ M$^2$s$^{-1}$ and it takes ~0.5 second to diffuse across a 50 μm channel. This is a too long mixing time for most chemical reactions. To overcome the limitations set by the diffusion processes, several microfluidic mixers were designed to generate chaotic advections, in which a transversal component of the velocity is produced thus enabling fast mixing.

Figure 3:
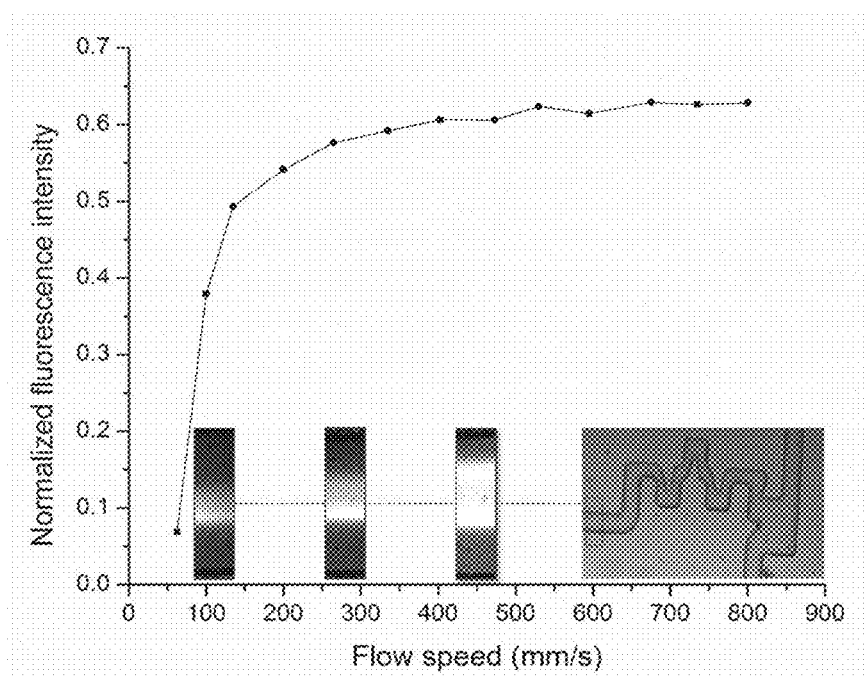
FIG. 3 is a plot of normalized fluorescence intensity as a function of flow velocity in the microfluidic device, detected immediately after the mixer, within the channel

A design of a passive microfluidic mixer based on a flow channel with "recirculating" alcoves arranged in a zigzag fashion was adapted (FIG. 2a). The channels are 20-75 μm in width and 15-50 μm in depth, their total volume is 1.8 nl and the flow speed range was 100-2000 mm/s. The mixing efficiency was tested by injecting two non-fluorescent reactants, which turn fluorescent upon mixing, as detailed in the experimental section. A plot of the fluorescent intensity of a small region of the channel immediately after the mixer, divided by that of a pre-mixed solution, as a function of flow speed is shown in FIG. 3. FIG. 3 is a plot of normalized fluorescence intensity after mixing two non-fluorescent solutions (which turn fluorescent after mixing) as a function of flow velocity in the microfluidic device, detected immediately after the mixer. The inserts show images of the mixer (right) with the fluorescence measured point (red rectangle), and fluorescence image at three different velocities.

The normalized fluorescence reaches a plateau of 0.62, where 0.58 is reached at a speed of about 250 mm/s, showing that above this velocity the mixing is good and practically constant. 100% is not reached because the fluid next to the walls does not flow and does not participate in the reaction. This is a typical characteristic of laminar flow.

The reaction progresses in the channel immediately after the mixer, where the flow and pressure were kept constant and controlled. In this setup the temperature was constant. The reaction time was proportional to the channel length and inversely proportional to the flow speed according to:

$$t_{sec} = x_{mm}/2 \cdot F_{mm/sec} \quad (3)$$

where F is the flow speed of the reactants (set by the pump rate and syringe cross section) and x is the channel length. The factor of 2 comes from combining two inlets into one channel. Thus, the minimal flow speed, 250 mm/s, in a 30 mm long channel corresponds to a maximal reaction time of 60 ms, and a flow speed of 1000 mm/s in a 10 mm long channel corresponds to 5 ms. In this calculation, the travel time from the outlet of the device to the cold metal trap and the freezing time was neglected because it is expected to be much shorter than 5 ms. In the current setup the different reaction times are determined by the flow rate.

Ejection of Solution from the Microfluidic Device.

The reaction mixture ejected from the microfluidic device has to overcome surface tension forces between the solution and the device. Furthermore, it should be sprayed as tiny drops, to facilitate their collection, and in a constant speed, independent of the flow speed in the reaction channel in order to minimize the deadtime. Accordingly, a feature which mixes the ejected reaction solution with a fast stream of nitrogen gas and sprays an aerosol or an assembly of small droplets out (FIG. 2c) was added to the microfluidic device. A needle, 100 μm i.d. and 5 mm long, was connected to the end of the channel, vertical to the device plane, through which the reaction mixture is ejected. (FIG. 2c, white arrow). This needle passes through a 4 mm diameter and 3 mm depth built-in cell, connected to a nitrogen gas source of a 50 μl/s flow (FIG. 2c, black arrow). The cell has a ring-shape opening around the outward-directed end of the needle with a total area of 5 mm$^2$. When the reaction mixture comes out of the needle it mixes with the nitrogen gas velocity (10 m/s) around it and it is sprayed out in tiny drops at a high speed. Without this unique ejection set-up the mixed liquid could not be ejected; without this unique ejection set up, the sample liquid accumulated as drops at the end of the needle.

Freezing and Sample Collection

In order to minimize losses of the frozen solution and improve its collection, freezing was done on a cold solid surface rather than the traditional ejection into a cold liquid. A setup was designed that allows the collection of all the samples corresponding to different reaction times in one continuous experiment. The samples were sprayed and frozen onto the upper side of a metal rotating plate placed close to the spraying needle (FIG. 2d).

The plate, 50 mm radius, was made of aluminum for its high thermal conductivity (~150 W/(m·K)). The use of copper, which has a higher thermal conductivity (~400 W/(m·K)) was avoided, because copper can form an oxide that can be scrapped with the sample and generate unwanted EPR signals. The plate was cooled to 80K by immersing its bottom in liquid nitrogen. To improve the heat transfer from the liquid nitrogen the plate bottom had a cone shape with grooves, which increased the contact area. The plate was placed 5 mm below the spraying needle, which is close enough to decrease its contribution to the deadtime by less than 0.5 ms, and is still far enough to prevent freezing of the microfluidic device. To decrease the freezing time, the sample should be sprayed directly on the plate rather than on a layer of frozen drops. Therefore, the plate rotates around its center at a speed correlated to the flow speed of the solution in the microfluidic channel (about 0.05 rad/s for a 500 mm/s flow). Samples corresponding to different time points, obtained with different flow rates, were frozen on the same radius but on different areas of the plate (see FIG. 8). In between time points the motor pump is stopped and the flow speed is readjusted. The first 2 μl of each time point are wasted by rotating the mixer such that no liquid reached the cold plate. This ensures that samples corresponding to different time points were not mixed. All samples were collected at the end of the experiment.

The frozen samples were collected into quartz capillaries. To enable holding the capillary without heating and thawing the frozen sample, one of its ends was connected to a polypropylene tip which has a low thermal conductivity (0.1 W/(m·K)). Since each sample was frozen as a collection of tiny drops, and due to the presence of glycerol (up to 30%), it was easy to collect the sample by holding the capillary with the plastic tip and poking it a few times into the frozen sample. After filling, the capillary was detached from its holder and immediately immersed into a liquid nitrogen container. The whole apparatus was placed in a box filled with nitrogen gas which provided a dry environment and prevented accumulation of frozen moisture (see FIG. 8).

Performance

Figure 4:
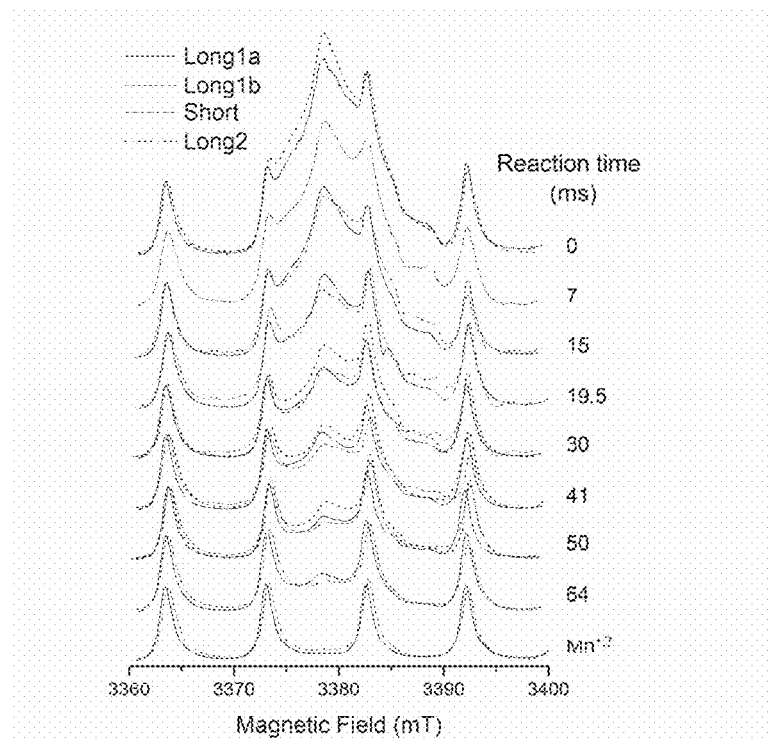
FIG. 4 is a W-band echo-detected –EPR spectra of RFQ samples collected at different reaction times.

The performance of the microfluidic RFQ apparatus was tested using the reduction of a nitroxide radical, TEMPOL with excess sodium dithionite, employing $Mn^{2+}$ as an internal standard. FIG. 4 shows a series of echo-detected EPR spectra of several RFQ experiments. FIG. 4 is a W-band ED-EPR spectra of RFQ samples collected at different reaction times as noted on the figure. The different shapes correspond to different experiments as follows: solid and dash lines are for the first and the second runs respectively of the "long1" device. dots line is for the "long2" device and dash dot line is for the "short" device. The $Mn^{2+}$ signal marked with "*" and the nitroxide signal marked with "o", were used in the calculation presented in FIG. 5.

The spectral region displayed shows four out of the six $Mn^{2+}$ lines of the central $|-1/2>-|1/2>$ transition. The reaction time was calculated from the length of the reaction channel and the flow velocity (see eq. 3). The spectra were normalized to the lowest field $Mn^{2+}$ line. The t=0 time point corresponds to the TEMPOL/$Mn^{2+}$ solution before mixing. To check reproducibility, several experiments were performed. Two were carried out on different days using the same device, with a reaction channel length of 25 mm. This device is referred to as "long1". Another experiment was carried out on a different device with the same dimensions, the device referred to as "long2". A third device with a reaction channel length of 10 mm was fabricated to access the shortest possible reaction time. This device was termed "short". Spectra corresponding to all of these experiments are shown in FIG. 4 and clearly show that the relative intensity of the nitroxide signal decreases with increasing reaction time.

The rate equation for the reduction of TEMPOL is:

$$\frac{d[\text{TEMPOL}]}{dt} = k[\text{dithionite}][\text{TEMPOL}] \quad (4)$$

where k is the rate constant. As dithionite is added in access the reaction behaves as a pseudo first order reaction with k'=k[dithionite]. This yields $$ln[\text{TEMPOL}]=ln[\text{TEMPOL}]_0-k't \quad (5)$$

where $[\text{TEMPOL}]_0$ is the concentration of TEMPOL at t=0.

Figure 5:
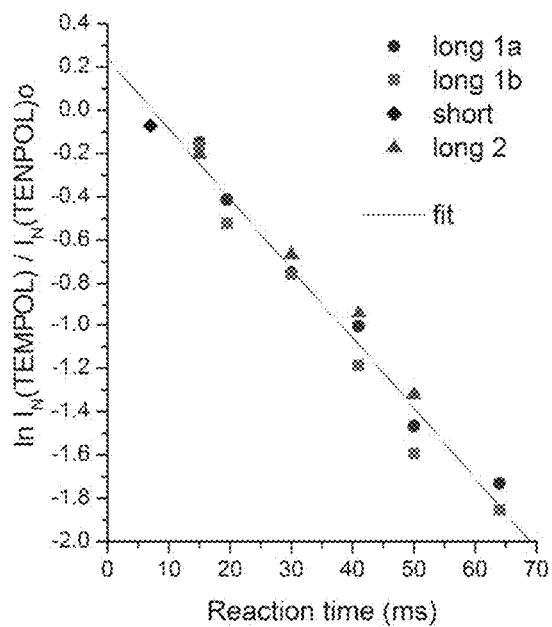
FIG. 5 is a plot of $I_N(TEMPOL)/I_N(TEMPOL)_0$ as a function of reaction time of the reduction of TEMPOL by dithionite.

[TEMPOL] is proportional to the normalized TEMPOL signal intensity, $I_N(\text{TEMPOL})=I(\text{TEMPOL})/I(Mn^{+2})$, taken at the field position where it reaches a maximum (see "o" mark in FIG. 4). FIG. 5 is a plot of $I_N(\text{TEMPOL})/I_N(\text{TEMPOL})_0$ as a function of reaction time of the reduction of TEMPOL by dithionite. The different shapes correspond to different experiments. The straight line is a linear fit of all points.

FIG. 5 presents $I_N(\text{TEMPOL})/I_N(\text{TEMPOL})_0$ as a function of the reaction time for all RFQ experiments carried out. A linear fit yields a slope of k'=$0.032\pm0.003$ ms$^{-1}$. This slope is similar to that obtained under the same reaction conditions using a commercial Biologic freeze quench apparatus ($0.04\pm0.005$ ms$^{-1}$). This indicates that reaction times calculated using eq. 3 describe well the actual reaction times. From k' k was obtained and was equal to: k=$0.64\pm0.06\times10^3$ s$^{-1}$M$^{-1}$. In Potapov et. al., the k value obtained from k', k=$(0.8\pm0.1)\times10^6$ s$^{-1}$M$^{-1}$ was miscalculated and is overestimated by a factor of $10^3$. Taking this error into account the reaction rate constant obtained from our microfluidic RFQ setup agrees well with this values.

At the starting of the reaction, t=0, $I_N(\text{TEMPOL})/I_N(\text{TEMPOL})_0=1$. A linear fit of the data shows that this value was reached at a reaction time of 7±2 ms. This is rather surprising as a reaction deadtime, arising from time spent in the mixer and the spraying and freezing time, should have led to a negative time, which actually represents the deadtime. A small error in the t=0 measurement would cause a shift up or down of the linear curve. In the present case the linear curve should be shifted down (i.e $I_N(\text{TEMPOL})_0$ is slightly under estimated), and the deadtime is estimated as being ~5 ms based on the flow rate and the channel length.

The volume of sample ejected and frozen on the quenching plate for each time point was about 10 µl and three capillaries for each time point were filled with ~2-3 µl. Thus, about 60% of the sample was used. The total volume needed for complete experiment of 7 time points in triplicates is 100-150 µl. This is an order of magnitude smaller than needed for a commercial RFQ for X-band measurements.

The flow in the microfluidic device was also tested with a 0.2 mM solution of a protein bovine serum albumin (BSA) that maybe more viscous than the solutions used herein above. With this BSA solution the device performed well, namely the solution was flowing regularly through the device.

CONCLUSION

A new rapid freeze-quench apparatus, based on microfluidic flow and a unique ejection and freezing systems, was designed and produced for high field EPR capillary samples. It was tested by using the standard and well characterized reduction of TEMPOL with dithionite. It was shown that the apparatus is highly efficient and reproducible, requiring a total of less than 150 µl TEMPOL solution for 7 time points (triplicates for each time point) with a resolution of a few ms and a deadtime ~5 ms. The apparatus featured an easy and fast operation; a complete experiment lasts about 15 min Such a system, combined with a variety of W-band high resolution EPR techniques such as ENDOR, DEER and ESEEM, open many new possibilities in mechanistic studies of enzymatic reactions, with emphasis on the structural transformations during the reaction. In biological systems the sample quantities are often highly limited and this has so far presented a considerable challenge for RFQ X-band EPR spectroscopy, thus preventing its widespread application. The combination of microfluidic RFQ devices, apparatuses and methods of this invention with high field EPR meet this challenge.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A microfluidic device comprising:
   a microfluidic channel comprising a first mixing part and a second reaction part, wherein said channel further comprises a first inlet and a second inlet;
   a product outlet, wherein said product outlet is attached to said microfluidic channel; and
   a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;

wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet.

2. The device of claim 1, wherein said first and second inlets are connected to an injection pump.

3. The device of claim 2, wherein said pump is used to inject said first and second materials through said inlets into said microfluidic channel.

4. The device of claim 2, wherein said pump controls the flow rate of said first and second materials within said reaction part of said microfluidic channel.

5. The device of claim 1, wherein the length of said microfluidic channel ranges between 0.5 cm and 4 cm.

6. The device of claim 1, wherein the height of said channel ranges between 10 µm and 100 µm.

7. The device of claim 1, wherein the width of said microfluidic channel ranges between 10 µm and 150 µm.

8. The device of claim 1, wherein said gas compartment is connected to a pressurized gas cylinder.

9. The device of claim 8, wherein said gas cylinder is used to deliver gas through said gas inlet channel, through said gas compartment and out of said gas outlet.

10. The device of claim 1, wherein the width of said reaction part of said microfluidic channel is constant.

11. The device of claim 1, wherein the width of said mixing part of said microfluidic channel varies along the length of said mixing part.

12. The device of claim 1, wherein said microfluidic channel, said inlets, said gas inlet channel, said gas compartment or a combination thereof are embedded in a first substrate and wherein said first substrate is covered by a second substrate.

13. The device of claim 12, wherein said first substrate comprises PDMS and said second substrate comprises glass.

14. The device of claim 1, wherein said microfluidic device comprises a translation element.

15. The device of claim 14, wherein said translation element translates said microfluidic device along an axis, around an axis or a combination thereof.

16. An apparatus for sample preparation, said apparatus comprising:
a microfluidic device comprising:
a microfluidic channel comprising a first mixing part and a second reaction part, wherein said channel further comprises a first inlet and a second inlet;
a product outlet, wherein said product outlet is attached to said microfluidic channel; and
a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;
wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet;
a cooling device comprising:
a translation element comprising a surface; and
a cooling element;
wherein said translation element contacts said cooling element,
wherein said translation element is cooled by said cooling element, and
wherein said product outlet of said microfluidic device is placed in proximity to said cooling device such that material can be transferred from said microfluidic device onto different areas on said surface of said translation element.

17. The apparatus of claim 16, wherein said translation element is motorized.

18. The apparatus of claim 17, wherein said translation element is movable around an axis, along an axis or a combination thereof.

19. The apparatus of claim 16, wherein the distance between said surface of said translation element and said product outlet, ranges between 2.5 mm and 7.5 mm.

20. The apparatus of claim 16, wherein said translation element comprises a rigid translation stage.

21. The apparatus of claim 16, wherein said translation element comprising a belt.

22. The apparatus of claim 16, wherein said cooling element comprises contacting said translation element with liquid nitrogen.

23. The apparatus of claim 22, wherein said translation element is a translation stage or a translation belt.

24. The apparatus of claim 23, wherein said translation stage is conical in shape such that the top of said surface of said translation stage is in the form of a circle, and wherein the bottom conical area of the translation stage which is smaller in diameter from said top of said surface is cooled by liquid nitrogen.

25. The apparatus of claim 16, wherein said microfluidic device comprises a translation element.

26. The apparatus of claim 25, wherein said translation element translates said microfluidic device along an axis, around an axis or a combination thereof.

27. A method of preparation of samples for analysis, said method comprising:
a. providing an apparatus for analysis, said apparatus comprising:
a microfluidic device comprising:
a microfluidic channel comprising a first mixing part and a second reaction part, wherein said channel further comprises a first inlet and a second inlet;
a product outlet, wherein said product outlet is attached to said microfluidic channel; and
a gas compartment surrounding at least a portion of said product outlet such that said gas compartment is coaxial with said product outlet, wherein said gas compartment is attached to a gas inlet channel, and wherein said gas compartment comprises a gas outlet proximal to said product outlet;
wherein upon introduction of a first material from said first inlet and a second material from said second inlet, said first material and said second material are mixed within said first mixing part, and wherein at least a portion of said materials react within said second reaction part and wherein upon ejection of mixed and at least partially reacted materials from said product outlet, a gas from said gas compartment is mixed with said materials thus facilitating ejection of said materials from said product outlet; and
- a cooling device comprising:
  - a translation element comprising a surface; and
  - a cooling element;
- wherein said translation element contacts said cooling element,
- wherein said translation element is cooled by said cooling element, and
- wherein said product outlet of said microfluidic device is placed in proximity to said cooling device such that material can be transferred from said microfluidic device onto different areas on said surface of said translation element.
  b. cooling said translation element using said cooling element;
  c. translating said surface of said translation element such that the top of said surface of said translation element remains at a constant vertical distance from said microfluidic device;
  d. injecting a first reactant solution from said first inlet and a second reactant solution from said second inlet such that said first reactant and said second reactant get into contact at said microfluidic channel and wherein said reactants are mixed within said mixing part and wherein said reactants at least partially react within said reaction part; and
  e. ejecting samples comprising at least partially reacted materials in a serial manner from said product outlet onto different areas of said surface of said translation element, wherein upon ejecting, the product solution is mixed with gas ejected from said gas compartment thus facilitating ejection of said product solution.

28. The method of claim 27, wherein the reaction time of said reactants within said reaction part is controlled by the injection rate of said reactants solutions.

29. The method of claim 28, wherein said reaction time is in the millisecond (ms) range.

30. The method of claim 27, wherein the number of samples transferred from said microfluidic device to said surface of said translation element ranges between 1 and 100.

31. The method of claim 27, wherein said microfluidic device is connected to a motor.

32. The method of claim 31, wherein said microfluidic device is moved horizontally with respect to said surface of said translation element.

33. The method of claim 32, wherein by horizontally moving said microfluidic device with respect to said surface of said translation element, said samples are transferred to different areas on said surface of said translation element.

34. The method of claim 33, wherein different samples ejected from said microfluidic device following different reaction times are serially collected on different areas of said surface of said translation element.

35. The method of claim 34, wherein said reaction time is controlled by injection flow rate.

36. The method of claim 27, wherein said sample ejected from said microfluidic device, is mixed with said gas to form tiny droplets.

37. The method of claim 36, wherein said sample comprising tiny droplets freezes upon contact with said surface of said cooling device.

38. The method of claim 37, wherein said sample freezes in small drops on said surface of said cooling device.

39. The method of claim 38, wherein the diameter of said drops ranges between 0.05 mm and 1 mm.

40. The method of claim 27, wherein following sample transferring onto said surface of said translation element, said samples are transferred to capillaries.

41. The method of claim 40, wherein said transferring into capillaries is automated.

42. The method of claim 40, wherein following transfer of samples to said capillaries, said capillaries are frozen in liquid nitrogen.

43. The method of claim 40, wherein said capillaries are transferred to an analysis instrument.

44. The method of claim 43, wherein said analysis instrument comprises an optical spectrophotometer, a mass spectrometer, an NMR instrument, an instrument for magnetic analysis, an electrical properties analysis instrument, a surface analysis instrument, a microscope, a chromatography tool, an electrophoresis set up or a combination thereof.

45. The method of claim 43, wherein said analysis instrument is electron paramagnetic resonance (EPR) instrument.

* * * * *